United States Patent [19]

Van Vlasselaer et al.

[11] Patent Number: 5,789,148
[45] Date of Patent: Aug. 4, 1998

[54] CELL SEPARATION COMPOSITION

[75] Inventors: Peter Van Vlasselaer, Sunnyvale; Varghese Palathumpat, Fremont, both of Calif.

[73] Assignee: Dendreon Corporation, Mountain View, Calif.

[21] Appl. No.: 570,120

[22] Filed: Dec. 11, 1995

Related U.S. Application Data

[63] Continuation-in-part of Ser. No. 299,469, Aug. 31, 1994, Pat. No. 5,474,687.

[51] Int. Cl.$^6$ .................................................. C12N 5/00
[52] U.S. Cl. .................... 435/2; 252/60; 252/302; 252/315.01; 252/315.2; 252/315.6; 424/529; 424/534; 435/261; 435/803; 427/503; 428/405
[58] Field of Search ............................. 435/2, 261, 803; 424/529, 534; 252/60, 302, 315.01, 315.2, 315.6; 427/503; 428/405

[56] References Cited

U.S. PATENT DOCUMENTS

| | | | |
|---|---|---|---|
| 4,927,749 | 5/1990 | Dorn | 435/2 |
| 4,927,750 | 5/1990 | Dorn | 435/2 |
| 5,310,572 | 5/1994 | Woodard et al. | 427/2.16 |
| 5,397,479 | 3/1995 | Kass et al. | 210/728 |

FOREIGN PATENT DOCUMENTS

| | | |
|---|---|---|
| 0574227 A2 | 6/1993 | European Pat. Off. |
| 3222452A1 | 6/1982 | Germany |

OTHER PUBLICATIONS

Pertoft et al., "Separation of Various Blood Cells in Colloidal Silica-Polyvinylpyrrolidon Gradients," *Experimental Cell Research*, vol. 50, pp. 355–368 91968).

Chaimberg, et al., "Graft Polymerization of Polyvinylpyrrolidone onto Silica," *Journal of Applied Polymer Science*, vol. 37, 2921–2931 (1989).

Olofsson, et al., "Separation of Human Bone Marrow Cells in Density Gradients of Polyvinylpyrrolidone Coated Silica Gel (Percoll)," *Scandinavian Journal of Haematology*, vol. 23, 254–262 (1980).

Laurent et al., "Physical Chemical Characterization of Percoll I. Partical Weight of the Colloid," *Journal of Colloid and Interface Science*, vol. 76, No. 1, pp. 124–132 (1980).

Palathumpat et al., "Enrichment of Committed and Uncommitted Human Hematopoietic Progenitor Cells Using the Density Gradient Based Simplesep Enrichment System," *Blood*, vol. 10, Supplement 1, p. 662A, abstract 2634 (1994).

Pertoft, H., "Separation of Blood Cells using Colloidal Silica–Polysaccharide Gradients," *Exp. Cell Res.* 46:621–623 (1967).

Pertoft, H., et al., "The Viability of Cells Grown or Centrifuged in a New Density Gradient Medium, Percoll (™)," *Exp. Cell Res.* 110:445–457 (1977).

Pertoft, H., et al., "Density Gradients Prepared from Colloidal Silica Particles Coated by Polyvinylprrolidone (Percoll)," *Analytical Biochem.* 88:271–282 (1978).

Wolff, D.A., and Pertoft, H., "Separation of HeLa Cells by Colloidal Silica Density Gradient Centrifugation," *J. Cell Biol.* 55:579–585 (1972).

*Primary Examiner*—Susan Wolski
*Attorney, Agent, or Firm*—Carol A. Stratford; Dehlinger & Associates

[57] ABSTRACT

Disclosed are a kit, composition and method for cell separation. The kit includes a centrifugable container and an organosilanized silica particle-based cell separation suspension suitable for density gradient separation, containing a polylactam and sterilized by treatment with ionizing radiation. The composition includes a silanized silica particle-based suspension for cell separation which contains at least 0.05% of a polylactam, and preferably treated by ionizing radiation. Also disclosed is a method of isolating rare blood cells from a blood cell mixture.

8 Claims, 5 Drawing Sheets

CELL SEPARATION COMPOSITION

This is a continuation-in-part of U.S. Ser. No. 08/299,469 filed Aug. 31, 1994, now U.S. Pat. No. 5,474,687.

FIELD OF THE INVENTION

The present invention relates to compositions, kits and methods for cell separation.

REFERENCES

Dorn, A. R., U.S. Pat. No. 4,927,749.
Pertoft, H. (1967) Exp. Cell Res. 46: 621–623.
Pertoft, H. et al. (1968) Exp. Cell Res. 50: 355–368.
Pertoft, H., et al. (1977) Exp. Cell Res. 110: 449–456.
Pertoft, H., et al. (1978) Anal. Biochem. 88: 271–282.
Wolff, D. A. and Pertoft, H. (1972) J. Cell Biol. 55: 579–585.

BACKGROUND OF THE INVENTION

Separation of cells and cellular components, long an important tool in basic research and diagnostic applications, is becoming increasingly important in the clinical setting. The growing significance and acceptance of cell transplantation methods, such as bone marrow transplantation, in human therapeutics has necessitated cell separation procedures that are not only rapid and reproducible but which also produce viable, safe, non-toxic cell compositions that are suitable for isolating cells that are relatively low in abundance (rare, i.e., comprise less than about 1% of total cells) from a cell mixture. For example, following chemotherapy for certain types of cancer, many patients now receive "stem cell transplants" which consist of an enriched fraction of hematopoietic progenitor cells isolated from various tissues, such as bone marrow, peripheral blood or cord blood. Such progenitor cells constitute about 1% of the total number of cells present in these tissues.

Density gradient centrifugation is a popular technique for separating and isolating cells and cellular components. This method exploits the phenomenon that cells partition in a defined density medium according to their buoyant densities. Such a medium may be a solution or a suspension of microparticles. Examples of media commonly used in density gradient separation include sucrose, dextran, bovine serum albumin (BSA), FICOLL diatrizoate (Pharmacia), FICOLL metrizoate (Nycomed), PERCOLL (Pharmacia), metrizamide, and heavy salts such as cesium chloride.

Exposure of cells to many of these media, however, results in impaired biological function of the cells and/or contamination of the preparation by toxic components. For example, BSA and FICOLL are known to cause unwanted cell aggregation at physiological pH. In addition, these media are not generally amenable to sterilization by autoclave or irradiation in "final form"—that is, in a concentration, ionic solution and container that is ready to use is isolating a particular cell type.

One cell separation medium that has been widely used in clinical as well as non-clinical protocols is PERCOLL (a registered trademark of Pharmacia Fine Chemicals). PERCOLL is a colloidal silica particle treated by a curing process to form a polyvinylpyrrolidone coating on each particle. PERCOLL is commonly used for separation and preparation of blood cells. While PERCOLL is fairly stable at physiological pH, there are some limitations to its general usefulness in isolating cells for therapeutic purposes. For example, the medium is difficult to sterilize, since it is not stable to autoclaving or ionizing irradiation after it is diluted in a physiological salt solution. These properties limit the usefulness of the product for clinical applications involving re-introduction of separated cells into humans or anywhere else that finally sterilized material is required.

U.S. Pat. No. 4,927,749 provides an organosilanized colloidal silica (OCS) particle (OCSP) preparation for density gradient separation that overcomes some of the problems discussed above. In particular, the medium is stable to sterilization by heat and ionizing irradiation when diluted in a physiological salt solution. However, it has been found that when sterilized by ionizing radiation, OCS particle preparations are toxic to certain rare cell types, such as dendritic cells, natural killer cells, natural suppressor cells, cytotoxic T cells, and in particular, hematopoietic progenitor (CD34$^+$) cells. Since final sterilization by ionizing radiation is preferred for certain applications, particularly those involving containment of the material in plastic consumable vessels, the use of this material for clinical applications is limited. Moreover, it has been found that the material induces clumping or aggregation of cells, thereby trapping rare cell types such as dendritic cells, natural killer cells, cytotoxic T cells, and in particular, hematopoietic progenitor cells. This results in significantly reduced yields of such rare cells in functional form. This is of particular concern in clinical applications where large numbers of rare cells having specific functions are needed for cell therapy—such as for certain malignant diseases, including cancer and viral infections. As an example, hematopoietic progenitor (CD34$^+$) cells are currently used in combination with myeloablative chemotherapy for the treatment of cancer.

The present invention provides colloidal silica cell separation media that improves the yield and functional potential of cells by reducing cell aggregation and cell toxicity. It is the discovery of the present invention that inclusion of a polylactam solution, such as the gamma polylactam polyvinylpyrrolidone (PVP), in the solution in which colloidal silica density gradient material is suspended markedly reduces cell aggregation entrapping of rare blood cells, resulting in improved yields. It is a further discovery of the present invention that inclusion of the polylactam prevents loss of clonogenic potential during density gradient isolation of certain hematopoietic progenitor cells by reducing the irradiation-induced toxicity of OCS solutions.

Hence, the present invention also provides a method for final sterilization of an OCS particle based cell separation medium and a cell separation kit in which the sterilized OCS medium is supplied in a consumable plastic container, such as in pre-filled plastic centrifuge vessels suitable for clinical cell separation.

SUMMARY OF THE INVENTION

In one aspect, the invention includes a kit that is suitable for use in cell separation applications. The kit includes a centrifugable container and an organosilanized colloidal silica (OCS) particle-based cell separation suspension. The suspension is sterilized by ionizing irradiation in the presence of at least about 0.05 percent polylactam. In a preferred embodiment, the container and OCS particle suspension are sterilized as a unit, e.g., with the suspension contained within the container. In another preferred embodiment, the polylactam is polyvinylpyrrolidone, present at a concentration between about 0.1 and 10% w/w.

The kit is particularly useful for isolation of rare blood cells, such as hematopoietic progenitor (CD34$^+$) cells, dendritic cells, natural killer cells, natural suppressor cells or cytotoxic T cells, from a cell mixture. In this case, the OCS cell separation suspension will preferably have a specific density that is approximately equal to that of the cell to be isolated. In preferred embodiments, $CD34^+$ cells are separated from a cell mixture consisting of peripheral blood mononuclear cells using an OCS particle-based cell separation medium having a specific gravity of 1.0605 gr/ml at an osmolality of 280±10 mOsm/kg $H_2O$, or from bone marrow cells using an OCS particle-based cell separation medium having a specific gravity of 1.0685 gr/ml at an osmolality of 280±10 mOsm/kg $H_2O$.

In a related aspect, the invention includes a silanized colloidal silica particle suspension composition for cell separation. The composition is treated with ionizing radiation, such as gamma rays or E-beam, in the presence of at least about 0.05% of a polylactam. In a preferred embodiment, the silica particle is an organosilanized colloidal silica particle. In another preferred embodiment, the polylactam is polyvinylpyrrolidone present at a concentration between about 0.1 and about 10 percent.

In yet another preferred embodiment, the particles comprising the composition are microspheres which have diameters that range from between about 0.003 and 50 microns.

The composition is particularly useful for isolating selected rare blood cell types from cell mixtures. Here, it is preferable to use an organosilanized colloidal silica particle suspension having a specific density that is approximately equal to that of the selected cell. For example, when the rare blood cell is a hematopoietic progenitor $CD34^+$ cell isolated from blood mononuclear cells, organosilanized colloidal silica particle suspension preferably has a specific density of 1.0605 gr/ml at an osmolality of 280±10 mOsm/kg $H_2O$. As another example, when the rare blood cell is a hematopoietic progenitor $CD34^+$ cell isolated from bone marrow cells, the organosilanized colloidal silica particle suspension preferably has a specific density of 1.0685 gr/ml at an osmolality of 280±10 mOsm/kg $H_2O$.

Other examples of rare cell types that may be isolated in accordance with the invention include dendritic cells, natural killer cells, natural suppressor cells and the like.

In another related aspect, the invention includes a method of sterilizing silanized colloidal silica particle-based cell separation media. Here the media is exposed to ionizing radiation, such as gamma rays or E-beam, in the presence of at least about 0.05 percent polylactam, and preferably between about 0.1 and 10% polyvinylpyrrolidone. This method is particularly useful for sterilizing organosilanized colloidal silica particle-based media.

In yet another related aspect, the invention includes a method of isolating selected rare blood cell types from cell mixtures. The method includes layering the cell mixture organosilanized colloidal silica particle-based cell separation medium containing at least about 0.05% polylactam, which is, in a preferred embodiment, polyvinylpyrrolidone present at a concentration of between about 0.1 and 10%. The separation medium has a density that is approximately equal to the specific density of the selected cell. The mixture is then centrifuged at a centrifugal force effective to pellet cells having specific densities greater than the specific density of the selected cell.

In a preferred embodiment of this aspect of the invention, the cell isolation method is carried out in a centrifuge tube having a constriction member positioned and constructed within the tube to retain fluid in the bottom portion of the tube below the constriction member, when the tube is inverted. In this embodiment, the cell-separation medium has a specific density that is within ±0.0005 gr/ml, and preferably ±0.0002 gr/ml, of the specific density of the selected cell type to be isolated. The cell separation medium is contained in the bottom portion of the tube extends above the constriction member to a level such that cells which are captured at an interface above the constriction member can be discharged by inversion of the tube. Such a tube may also include a closed top and ports for introduction of fluid material and for venting, as well as a closed fluid channel that communicates a port with the bottom of the tube below the constriction member.

In the foregoing method embodiments of the invention, it is understood that the OCS-based cell separation density gradient may be sterilized by ionizing radiation in the presence of poly-vinylpyrrolidone. Such methods as described above are particularly preferred for use in isolating functional hematopoietic progenitor cells from mixtures of blood cells or bone marrow cells, under the conditions described above.

In yet another preferred embodiment, silanized silica particles having attached cell antigen-specific binding molecules are added to the cell mixture prior to centrifuging. Such particles serve to bind to and increase the density of selected cells in the mixture.

In still another related aspect, the invention includes a composition that is particularly suitable for used in isolating a functional rare blood cells from a cell mixture. The composition is an organosilanized colloidal silica particle-based cell separation medium that contains at least about 0.05% polylactam, preferably polyvinylpyrrolidone present at a concentration of between about 0.1 and 10 percent. The composition preferably has a specific density that is approximately equal to the specific density of the selected cell.

DETAILED DESCRIPTION OF THE INVENTION

Figure 1:
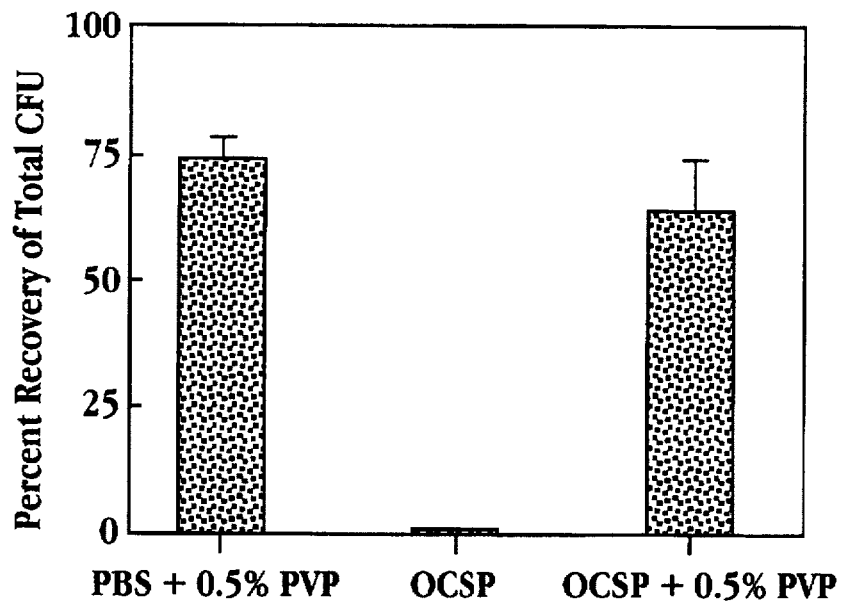
FIG. 1 shows recovery of functional hematopoietic progenitor cells (colony forming units, CFU) after incubation with gamma-irradiated 0.5% PVP in PBS, gamma-irradiated OCS particle-based density gradient material (OCSP), or gamma-irradiated OCS particle-based density gradient material supplemented with 0.5% PVP (OCSP+0.5% PVP)

The invention encompasses several aspects of a cell density gradient separation medium suitable for separation of cells, and particularly for separation or isolation of cells to be transplanted into humans. As described in the sections that follow, the invention is based on the discovery that cell toxicity is reduced when a solution of a gamma polylactam such as polyvinylpyrrolidone is added to a suspension of organosilanized colloidal silica (OCS) particles used in density gradient separation of the cells.

In particular, inclusion of the polylactam prevents loss of clonogenic potential in rare populations of hematopoietic progenitor cells that occurs when such cells are suspended in a suspension of organosilanized silica particles that has been sterilized by ionizing radiation. This form of sterilization is desirable for providing final sterilization of devices used in clinical applications, for example, disposable centrifuge containers pre-filled with density gradient material. In addition, the present invention includes the discovery that inclusion of polylactams such as polyvinylpyrrolidone in the density gradient medium also reduces aggregation and loss of clonogenic potential of hematopoietic progenitor cells that occurs without ionizing radiation.

I. Definitions

"Colloidal silica" refers to an aqueous suspension of colloidal particles formed by polymerization of monosilicic acid from $SiO_2$ dissolved in water.

"Organosilanized colloidal silica (OCS) particles" refers to a colloidal silica composition to which is covalently linked an organosilane coating. U.S. Pat. No. 4,927,749 is incorporated herein by reference in its entirety for its description of how to prepare such a composition.

"Rare blood cells" refers to cells that are derived from hematopoietic progenitor cells, including such cells, and which constitute less than about 1% of the total white blood cell (WBC) count in the blood of a healthy individual. Examples of rare blood cells include $CD34^+$ hematopoietic progenitor cells, which constitute about 1% of WBC's, natural killer cells, Natural suppressor cells, dendritic cells, and cytotoxic T cells. Also included in this definition are cells from exogenous sources, including circulatory fetal cells in maternal blood.

"Cell toxicity", "toxic to cells", and similar phrases herein refer to any diminution in cell viability or biological function that is measurable in a cell population. With reference to the hematopoietic progenitor cells described herein, the term most commonly refers to diminution in clonogenic potential, as evidenced by reduced yield of cells capable of forming hematopoietic colonies (CFU).

A "polylactam" is a polymer containing pendant lactam (cyclic amide) groups attached to the polymer backbone. The polymer may be a homopolymer or a copolymer. The pendant lactam groups will generally have ring sizes containing from 3–6 carbon atoms. One preferred type of polylactam for use in the present invention is a polyvinyl lactam, such as polyvinylpyrrolidone, which has a 4 carbon ring.

"Dendritic cells", or "DC" are matured DPC, which are negative for expression of CD3, CD4, CD8, CD14, CD16 and CD20, positive for expression of HLA-DR (i.e., class II MHC). Dendritic cells typically have a dendritic cell morphology—that is, they are large veiled cells which extend dendrites when cultured in vitro.

II. Cell Separation Medium

A. Silanized Silica Particles

The methods and compositions described herein are applicable to a number of uses of silanized silica particles in conjunction with cell separation. The particles can be silanized by any of a number of methods known in the art. U.S. Pat. No. 4,927,749, incorporated herein by reference, describes preparation of OCS particles that are particularly useful in preparing the compositions used in the present invention. In one embodiment, OCS particles ranging in size from 3–22 nm, and particularly from 13–18 nm, form a stable suspension that acts as a density gradient medium for separating heterogeneous mixtures of cells on the basis of buoyant density.

In addition to forming density gradient materials, silanized silica particles can also be used in other aspects of cell separation. For example, particles used in certain positive or negative selection steps may be treated in accordance with the methods described herein. Such particles are typically silanized silica microspheres or beads having diameters ranging up to about 50 microns, and conventionally, within the range of about 1–5 microns. Such particles are silanized according to methods well known in the art, for example, using 3-aminopropyltriethoxysilane, (3-iodopropyl) trimethoxysilane, [1-9trimethoxysilyl)-2(m- (or p)chloromethyl)phenyl] ethane, or 3-glycidyl-oxypropyltrimethoxysilane (GPMS). Typically, these particles have as covalent attachments specific antigen binding molecules, such as antibodies, lectins or other cell binding agents. When added to a cell mixture, the microspheres bind to cells having a specific target antigen or antigens, and modify (increase or decrease) the density of the cells.

Polyvinylpyrrolidone (PVP) has been added to suspensions of non-silanized colloidal silica particles (Pertoft, et al., Exp. Cell Res. 46: 621–623 (1966); Pertoft, et al., Exp. Cell Res. 50: 355–368 (1968); Wolff, et al., J. Cell Biol., 55: 579–585 (1972); Pertoft, et al., Exp. Cell Res., 110: 449–457 (1977)). However, free PVP in solution has been reported to have undesirable effects on some cell types (Pertoft, et al., Exp. Cell Res. 50: 355–368 (1968)). This lead to development of a thermal curing process that produces a PVP coating adsorbed to the colloidal silica particle, and which is substantially free of free PVP. (Pertoft, et al., Anal. Biochem. 88: 271–282 (1978)). This composition is commercially available as PERCOLL (registered trademark of Pharmacia Fine Chemicals, Piscataway, N.J.).

However, PERCOLL cannot be sterilized by conventional means (autoclaving or ionizing radiation) when diluted in a physiological salt solution at a final concentration suitable for cell separation. This limits its usefulness in applications that require a finally sterilized density gradient material in a physiological medium.

As noted above, a colloidal silica particle-based preparation having a covalent organosilane coating has been found to have utility in separating various blood cells (U.S. Pat. No. 4,927,749). The organosilane coating reduces cell toxicity and eliminates aggregation of the colloidal silica particles themselves in the presence of physiological salt and protein. However organosilane-coated colloidal silica (OCS) particles have certain disadvantages when used to separate or purify specific rare blood cells from blood and other sources. As is described in greater detail below, such particles may be toxic to and/or reduce the recoverable yield of such rare cells. This is exemplified below in conjunction with isolation of an important hematopoietic progenitor cell characterized antigenically as a $CD34^+$ cell, which can be isolated from blood or bone marrow. Specifically, as is demonstrated by experiments carried out in support of the present invention and detailed in the sections that follow, these rare blood progenitor cells aggregate or otherwise increase in density, when suspended in OCS particle-based density material. Moreover, though autoclaving is possible, sterilization of an OCS particle-based suspension by ionizing radiation results in a composition that is toxic to these cells. Experiments demonstrating these results and the improvements provided by the discoveries of the present invention are presented in the sections that follow.

B. Protection by Polylactams against Radiation-induced Toxicity of Silanized Silica Particles There are a number of methods of sterilizing density gradient materials. Silica-particle based density gradient materials can be sterilized by autoclaving or by filtration, according to methods known in the art. One method that is particularly useful is sterilization by ionizing radiation. This method may be preferred when the prepared density material is to be dispensed in plastic consumable containers, such as in pre-filled centrifuge tubes, bags, or syringes and the like for clinical separations, or when it is to be dispensed in any heat-sensitive containers, such as plastic bottles. Unlike other methods of sterilization, irradiation-based sterilization methods can be carried out on the end-product container as a one-step process. That is, when it is necessary to sterilize both a container and a liquid or suspension in the container, there is no need to separately sterilize the container itself, as is required when filtration methods are used, and there is no need to transfer the material from a sterilizing vat to individual containers, as would normally occur with heat-sterilization (autoclave).

Techniques for sterilizing medical devices by ionizing radiation are known in the art. Commonly used methods applicable to the present invention include gamma irradiation and electron beam (E-beam) radiation. While each of these methods involves a different type of energy source, both methods involve passing the device through a radiation field to achieve a specific radiation dose to the device. Typically, sterilization of a medical device requires a dose of between 10 and 30 kiloGrays (kGy). However, as described below, when either of these methods is used to sterilize organosilanized colloidal silica, the material becomes toxic to hematopoietic cells, unless a polylactam such as PVP is present in the particle suspension during irradiation.

The polylactams used in the present invention are preferably soluble polymers such as the KOLLIDON series of polyvinylpyrrolidones (BASF, Ludwigshafen, Germany). These polymers are generally available in polymer molecular weights ranging from 2000 to 350,000, and are rated by their intrinsic viscosities or "K values." In experiments carried out in support of the present invention, preparations having average molecular weights of about 10,000 were used. Polyvinylpyrrolidone is known to be sensitive to gamma-irradiation. Generally, an increase in average polymer molecular weight is observed when a solution is exposed to 10–50 kGy of gamma radiation. Accordingly, the manufacturer does not recommend that the material be exposed to ionizing radiation for purposes of sterilization (KOLLIDON: Polyvinylpyrrolidone for the Pharmaceutical Industry, BASF Aktiengesellschaft, Feinchemie, D67056 Ludwigshafen).

In experiments carried out in support of the present invention, it has been found that incubation of peripheral blood mononuclear cells (PBPC) in an OCS particle-based density gradient material sterilized by filtration (0.2 μm) or by heat-sterilization (autoclave, 15 min. at 120° C.) does not significantly affect recovery of viable hematopoietic progenitor cells, as assessed by a functional cell assay, the colony forming unit (CFU) assay, which measures the potential of such cells to form hematopoietic colonies. However, when an OCS particle-based density gradient material was sterilized by exposure to gamma radiation (2.5–3.5 megaRads) according to standard methods, cells incubated in this medium according to the protocol described as Method 2 in Example 4 (incubation with OCS+0.5% PVP for 30 minutes plus 10 minutes centrifugation time) exhibited reduced functional activity (to approximately 25% of added CFU activity). The result was even more striking for cells treated according to the protocol described as Method 4 in Example 4 where no culturing step was included. Here, cells were incubated for 30 minutes in an OCS particle-based density gradient material. OCS particles+0.5% PVP or buffer +0.5% PVP, followed by centrifugation for 10 minutes followed by 24 hours incubation in ISCOVES medium supplemented with 10% fetal cell serum. Inclusion of 0.5% PVP in the OCS particle suspension during preparatory sterilization and resulted in a recovery of about 65% of the CFU added (FIG. 1), while those cells incubated in an OCS particle-based density gradient material alone exhibited only about 1% of original functional activity. While this experiment used cells derived from PBMC, bone marrow- and cord blood-derived cells will exhibit the same susceptibilities.

Figure 2:
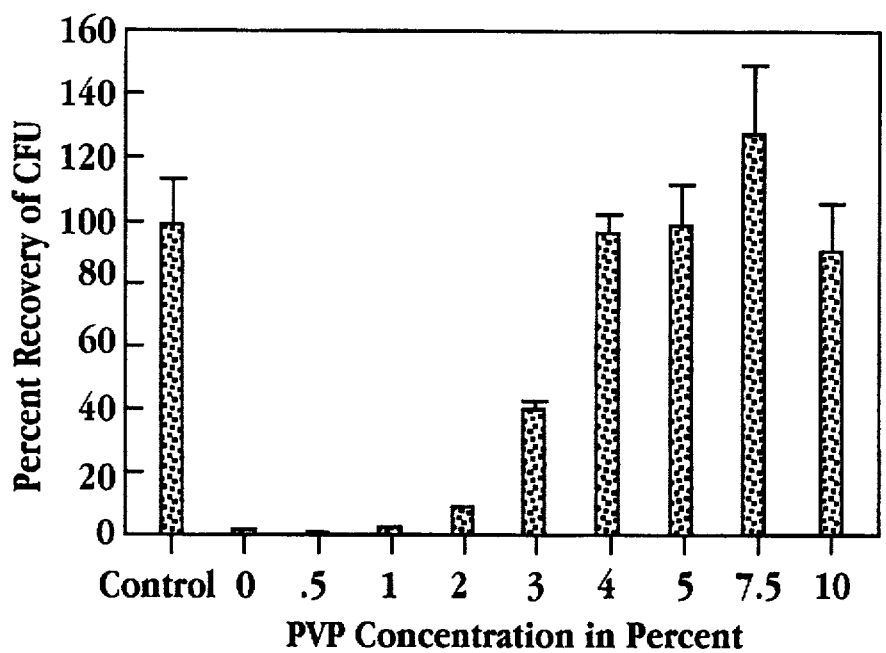
FIG. 2 shows the effect of various concentrations of PVP present during sterilization of OCS particles (OCSP) on gamma-irradiation-induced restriction of hematopoietic progenitor cell function (CFU)
Figure 3:
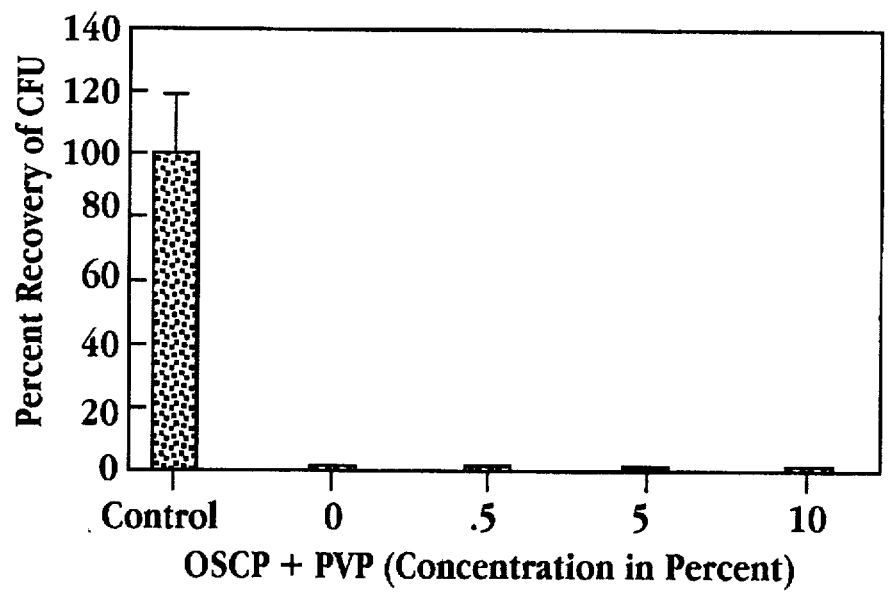
FIG. 3 shows the effect of various concentrations of PVP added after gamma-irradiation of OCS particles (OCSP) on hematopoietic progenitor cell function (CFU)

The amount of polylactam required to provide protection to cells was investigated in further experiments carried out in support of the present invention. FIG. 2 shows that an OCS particle-based density gradient material was supplemented with various concentrations of PVP prior to gamma irradiation (2.5–3.5 megaRads). In this study, PBPC cells were processed according to the protocol identified as Method 6 in Example 4 (incubation in presence of density gradient suspension and 10% fetal calf serum for 24 hours at room temperature). PVP in excess of 3% final concentration in the density gradient medium provided significant protection against irradiation-induced toxicity at the dose (2.5–3.5 megaRads) of radiation applied. Addition of PVP after sterilization of the medium did not provide a similar protective effect (FIG. 3).

From the foregoing it will be apparent that the present invention includes an improved cell density gradient composition for use in separation of rare blood cells. The product composition is a silanized silica particle treated by the process of ionizing radiation in the presence of at least about 0.05% polylactam, and more specifically, between about 0.1 and 10% polyvinylpyrrolidone. Such a composition is particularly well suited for isolating rare blood progenitor cells, such as hematopoietic progenitor (CD34$^+$) cells, that are sensitive to exposure to irradiated organosilanized colloidal silica.

C. Polylactam Improvement of Recovery of Rare Blood Cells from Density Gradients In accordance with another aspect of the invention, it has been discovered that supplementation of a suspension of organosilanized silica particles with 0.05% (wt/vol) polylactam results in improved yields of rare blood cells in functional form. More specifically, inclusion of the polylactam prevents aggregation or clumping of the cells to provide a cell composition having a more uniform density profile and improved functional properties. In comparison to cells isolated in OCS density gradient material in the absence of a polylactam, such compositions are characterized increased recovery of rare cells in enriched fractions, and increased recovery of rare cells having clonogenic potential.

Figure 4:
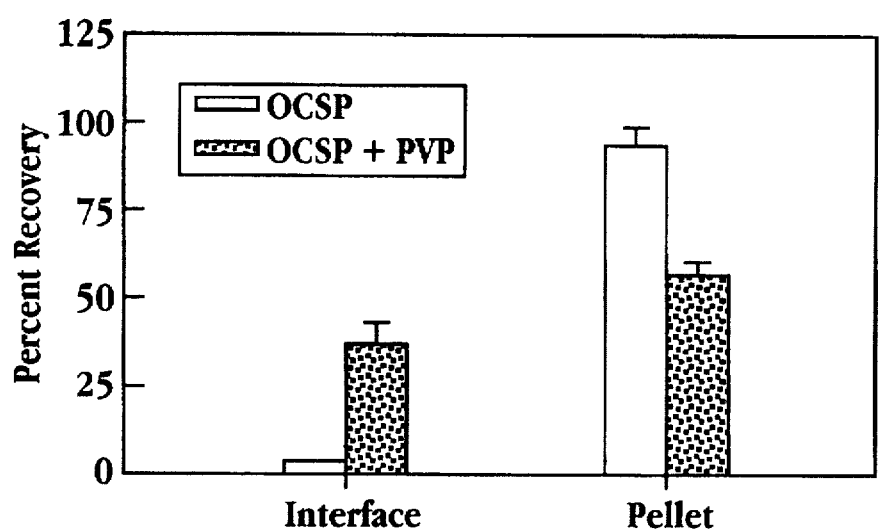
FIG. 4 shows the distribution of PBPC cells in interface and pellet fractions of density gradients formed from colloidal silica particles in the absence (OCSP) and presence of 0.5% PVP (OCSP+PVP)
Figure 5:
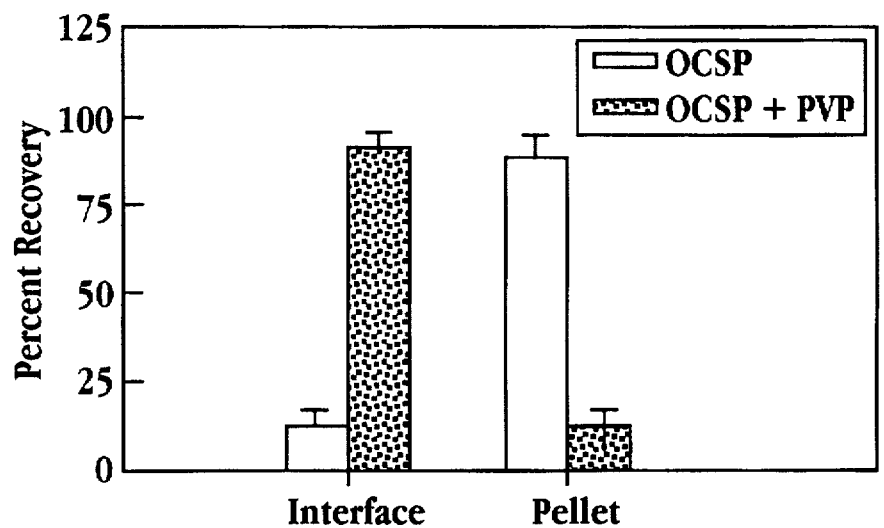
FIG. 5 shows the distribution of hematopoietic progenitor cells ($CD34^+$) cells in interface and pellet fractions of density gradients formed from colloidal silica particles (OCSP) in the absence and presence of 0.5% PVP (OCSP+PVP)

By way of example, FIGS. 4 and 5 show the results of experiments in which PBPC isolated according to standard methods were loaded onto an organosilanized colloidal silica density gradient (OCS particle-based density gradient material, 1.0605 g/ml, 280 mOsm/kg H$_2$O, pH 7.4) and centrifuged according to the protocol detailed in Example 3. FIG. 4 shows that in the absence of PVP, most of the cells present in the starting material were recovered from the pellet. Visual inspection revealed that this pelleting of the cells appeared to be the result of aggregation or clumping of the cells. In contrast, when the OCS density material was supplemented with 0.5% PVP, a higher percentage of cells remained at the interface, as would be predicted based on the pre-determined density of these cells.

This observation was more pronounced when the same cell preparations were analyzed for the presence of hematopoietic progenitor cells ($CD34^+$ cells) according to methods detailed in Examples 5 and 6 (FACS and CFU analysis). The results shown in FIG. 5 show that in the absence of PVP, about 90% of the $CD34^+$ cells migrated to the pellet. The presence of 0.5% PVP in the density gradient suspension reversed this pattern. Here, most of the $CD34^+$ cells remained at the interface, as is desirable for purposes of isolation and enrichment of such cells for transplantation and other clinical purposes.

In view of the foregoing, it can be appreciated that the present invention includes not only a density gradient composition that improves recovery of rare blood cells, but also a method of isolating functional rare blood cells, and particularly cells such as hematopoietic progenitor cells, dendritic cells, natural killer cells, natural suppressor cells and the like from a cell mixture. Generally, hematopoietic progenitor cells can be isolated from bone marrow, cord blood, or from peripheral blood samples. In either case, it is desirable to mobilize the cells by treatment with agents such as granulocyte colony stimulating factor (G-CSF), VP-16, or a combination of the two factors, according to known protocols. Following such treatment, the patient is subjected to apheresis to collect PBPC or to bone marrow aspiration to collect bone marrow.

According to the method disclosed herein, the collected cells are layered onto an organosilanized colloidal silica particle-based cell separation density gradient suspension that has a specific density that is approximately equal to that of the cells to be isolated and includes at least about 0.05% PVP, and more preferably, at least about 0.5% PVP. The suspension is then centrifuged to pellet cells having a specific density that is greater than the specific density of the selected hematopoietic cell. Such a density gradient composition also has the advantage of being capable of being sterilized by ionizing radiation according to the methods described in Part B, above.

The foregoing method can also be enhanced by adding to the initial cell mixture a suspension that includes an organosilanized silica particle to which is attached a cell antigen-specific binding molecule for negative or positive selection. As an example of negative selection, the antigen-specific binding molecule might bind an unwanted cell type in the cell mixture to cause the cell to migrate to the pellet.

III. Sterilized Cell Separation Kit

An important application of the discovery of the present invention is a sterile kit for cell separation. Such a kit is particularly useful for clinical cell separations. Such a kit will commonly include a centrifugable container and a density gradient material for separating cells, which has been sterilized as a filled unit by exposure to ionizing radiation. The centrifugable container will commonly be a consumable, disposable unit formed from plastic, such as polypropylene, polycarbonate, polysulfone, polymethylpentene, polyethylene, polyallomer, polystyrene and the like. However, as discussed below, the advantages of sterilizing the kit as a pre-filled unit also makes this procedure desirable for kits that include tubes formed from other materials. In a preferred embodiment, the container will be closed, as illustrated below, to facilitate aseptic collection of starting material and preservation and manipulation of the material in a sterile condition.

Figure 6:
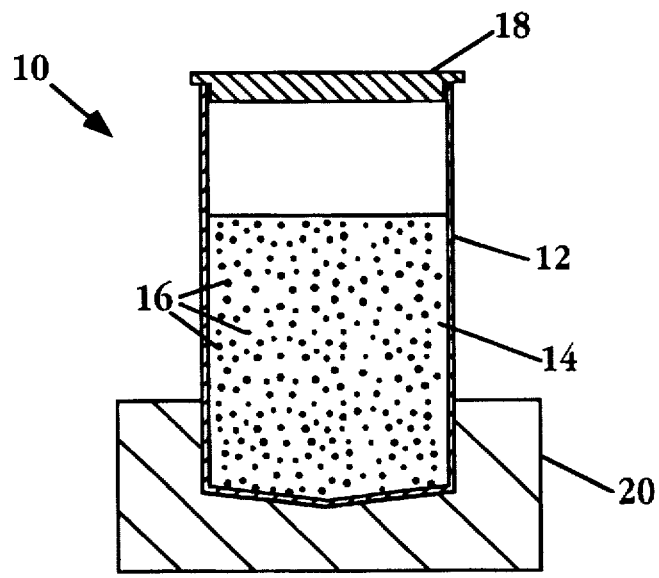
FIG. 6 shows a sterilized centrifuge kit assembled in accordance with the invention.

FIG. 6 illustrates a kit 10 formed in accordance with the present invention. As illustrated, kit 10 includes centrifuge tube 12 shown here filled with density gradient material 14. The density gradient material is formed by a suspension of organosilanized silica particles, such as particles 16. Also included in the density gradient material is at least 0.05% PVP, and preferably between about 0.1% and 10% PVP to reduce toxicity to rare blood cells isolated in the kit, thus improving yield of such cells in the kit.

The container and the density gradient contained within are sterilized by ionizing radiation, such as gamma irradiation or E-beam. The resulting kit may also include a protective cover, such as cap 18 to protect the contents of the tube from contamination after sterilization. The kit may also include a stand, such as tube-holder 20, to prevent displacement of tube contents during shipment and storage.

Kits as described above can be prepared according to the specifications required for separation of a number of cell types. The size of tube used, as well as its structural and chemical resiliency can be varied within the confines of the present invention for use in ultracentrifugation as well as in relatively low-speed centrifugation applications as described herein. Such modifications will be apparent to persons skilled in the art.

Similarly, the kit may be designed for different cell types by varying the composition of the density gradient material. Example 9 describes a kit that is particularly formulated for isolation of $CD34^+$ hematopoietic progenitor cells from PBPC. In the embodiment described, the OCS particulate density gradient suspension is adjusted to a specific density of 1.0605 g/ml and an osmolality of 280 mOsm/kg $H_2O$. This density is approximately equal to the density of the desired $CD34^+$ cells, so that upon centrifugation, these cells will "float" at the interface between the loading material and the density material present in the tube.

It is appreciated that enrichment of other rare blood cell types, such as dendritic cells, cytotoxic T cells, natural killer cells, natural suppressor cells and fetal nucleated cells can be achieved by adjusting the specific density and osmolality of the density gradient material. Such adjustment can be made so that the desired cells will then either float or pellet, according to the density of the desired cells and the relative density of unwanted cells present in the cell mixture from which the cells are to be isolated.

A preferred centrifuge tube configuration for use in the kit and method of the invention is one that has a constriction member disposed within the tube, forming a "cell-trap." Such a tube is described in co-owned, co-pending parent application U.S. Ser. No. 08/299,469, allowed as U.S. Pat. No. 5,474,687, which is incorporated herein by reference in its entirety. A modified form of this tube is illustrated as part of a closed system in FIG. 7 herein, described below.

In the cell-trap tube, the constriction member is positioned and constructed to retain fluid in the bottom portion of the tube below the constriction member when the tube is inverted. The tube also includes cell-separation medium that is contained in the bottom portion of the tube and which extends above the constriction member to a level above the opening formed by the constriction member. Cells that are captured at an interface between the cell-separation medium and a lower-density medium, after centrifugation, are discharged with the lower-density medium when the tube is inverted. This facile means of collection of cells is particularly convenient in the context of the present invention, where minimal manipulation of the cells is desirable.

Figure 7:
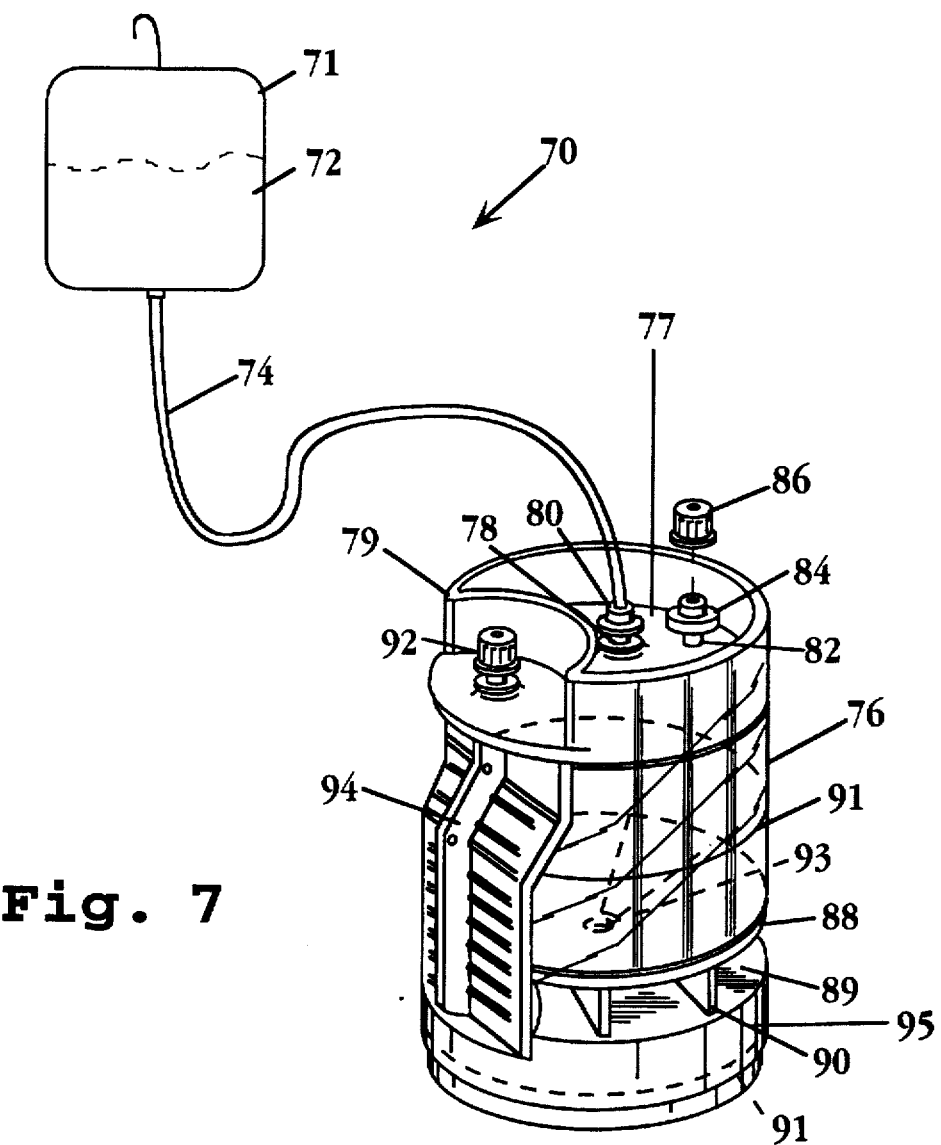
FIG. 7 shows a closed system centrifugation device suitable for inclusion in a kit of the invention.
Figure 8:
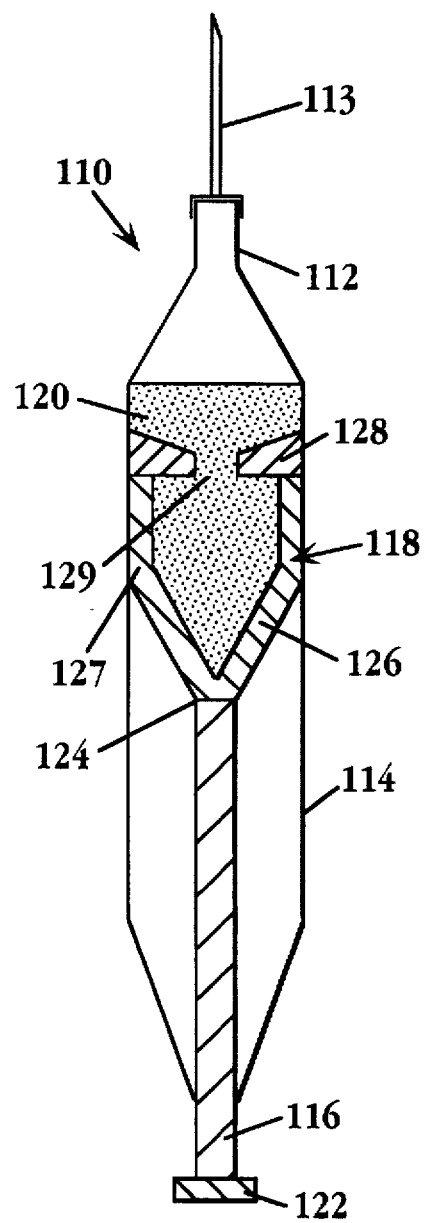
FIG. 8 shows a centrifugable syringe configuration of the kit.

It is also appreciated that, for clinical applications, the kit can be configured as a "closed system" to restrict access of external pathogens to the biological materials. FIGS. 7–8, described below, show exemplary closed system configurations that represent some of the numerous closed system configurations that can be used in kits of the present invention. Persons skilled in the art will appreciate other similar embodiments that will function in kits in accordance with the invention.

FIG. 7 shows a centrifugable bucket having a constriction member incorporated into a closed system. As illustrated, closed system 70 includes a reservoir 71, shown as a sterile bag, containing blood 72 previously collected by known techniques connected by sterile connecting tubing 74 to centrifuge tube 76, illustrated as a "bucket" style centrifuge tube having a closed top 77. The closed top will have at least one, and preferably at least two entry ports, useful for introduction and removal of sample, and for venting, as described below. In the embodiment shown, solid ridge 79 protruding upward from closed top 77 is included to form a protective barrier for the entry ports, and as an attachment point for a protective, removable lid for the apparatus that serves to reduce potential contamination during shipping and storage.

With further reference to FIG. 7, tubing 74 is attached to bucket tube 76 through entry port 78, adapted with fitting 80, which may be any type of locking tip adapted for sterile connection, for example, a Luer-Lock™ syringe connector. Alternatively, fitting 80 may be a sterile septum adapted for connection with sterile fluid bags and tubes, for example a SAFSITE™ small wire extension set with reflux valve and Spin-Lock™ adaptor available from Burron Medical Inc., Bethlehem, Pa. To facilitate fluid flow into centrifuge tube 76, the bucket contains air vent entry port 82. As shown, air filter 84 is attached to entry port 82 to prevent contamination. Also illustrated is cap 86 which covers air filter 84.

In accordance with a preferred embodiment of the invention, bucket tube 76 includes constriction member 88 forming central opening 93. Although a number of configurations are possible, as illustrated, constriction member 88 is funnel shaped on its upper surface. As illustrated, constriction member 88 is formed integrally with bucket 76 forming an indentation 89 on the outer surface of the tube. The constriction member is supported by supports 90 to prevent compression during centrifugation. The bucket also contains OCS particle density gradient material 91 disposed in the tube both above and below constriction member 88. The entire system as illustrated is sterilized by gamma irradiation or E-beam according to standard methods.

An added feature of bucket tube 76 is entry port 92. This entry port communicates via closed fluid channel 94 with the bottom portion 95 of tube bucket 76. The entry port and channel are used to fill the lower portion of the tube 95, for example, with density gradient cell separation medium prior to sterilization. Alternatively, the port and channel may be used to remove materials, including cell pellet materials, from the bottom of the tube following centrifugation. This feature of the tube is neither required by nor restricted to the closed system context in which it is illustrated.

Fluid flow from reservoir 71 into bucket 76 can be initiated by applying suction on air vent entry port 82, or it may be initiated by other means known in the art, including gravity. The rate of flow is adjusted, either by altering the pressure head between the two containers or by regulating a valve positioned in the tube or at the entry port at a point between reservoir 71 and entry port 78. Flow rate is optimally regulated to fill or partially fill the upper portion of bucket 76, above the level of the density gradient solution. When sufficient fluid sample has entered the tube, flow can be terminated by any of a number of means known in the art, such as regulation by a valve or by lowering of pressure head. The tubing is then removed from the bucket, port 78 is sealed, and the bucket is subjected to centrifugation as described above.

In another preferred embodiment that is particularly useful in carrying out the method of the present invention, the constricted tube may take the form of a centifugable syringe, such as centrifuge syringe 100 illustrated in FIG. 8. As illustrated, centrifuge syringe 110 includes a specimen container 114 with a central orifice surrounded by fitting 112 adapted for receiving a needle 113, a handle 116 and a plunger 118. Fitting 112 may be any type of locking tip adapted to hold a needle, for example, a Luer-Lock™ syringe tip. Alternatively, fitting 112 may be a sterile septum adapted for connection with sterile fluid bags and tubes, for example a SAFSITE™ small wire extension set with reflux valve and SpinLock™ adaptor available from Burron Medical Inc., Bethlehem, Pa.

Handle 116 further preferably comprises knob 122 and a removable connection 124 to plunger 118. As shown, plunger 118 is single piece, machined or molded from a plastic material. The plunger preferably has a funnel-shaped bottom wall 126 that is removably connected to the handle at connection 124. Side wall 127 preferably closely matches the container wall to permit sliding movement but still provide an essentially fluid-tight barrier therearound. A top wall is formed by constriction member 128, which defines central opening 129. Alternatively, the outer diameter of side wall 127 may be slightly undersized to facilitate sliding and an o-ring seal provided between side wall 127 and container 114. Removable connection 124 may take the form of, for example, a screw fitting or a snap-fit. Preferably, connection 124 also provides for reattachment of handle 116.

The plunger 118 is filled with OCS particle density gradient material 120 and sterilized by ionizing radiation before the introduction of a specimen. Preferably, the density gradient material is filled to a level above the constriction member, or at least above the top of opening 129. For example, when using a standard 50 ml syringe, having an inner diameter of about 2.8 cm, the gradient material is preferably filled to a level about 1 mm or more above constriction member 128, so that the interface forms above constriction member 128.

In a related embodiment, it will be understood that the above-described centrifugable-syringe configuration of the tube is particularly well suited for use in a closed system as described above.

Another configuration of the device that is suitable for use in the invention is a centrifugable bag. Such a configuration is particularly suitable for use in processing clinical blood samples which can be collected directly into the bag.

The following examples illustrate, but are in no way intended to limit the present invention.

EXAMPLES

Materials

A. Density Gradient Materials

Organosilanized colloidal silica particles (size range: 15–30 nm) used in the examples below were prepared according to the methods described in U.S. Pat. No. 4,927,749 using gammaglycidoxypropyl-trimethoxysilane (GPMS). Polyvinylpyrrolidone (PVP-10) was obtained from Sigma (St. Louis, Mo.).

B. Monoclonal Antibodies

Monoclonal antibodies (mAb) directed against surface antigens specific for hematopoietic progenitor cells (anti-CD34; anti-HPCA-2) and leukocytes (anti-CD45; anti-HLE-1) were obtained from Becton Dickinson, Inc. (San Jose, Calif.). The different monoclonal antibodies were directly labeled with fluorescein isothiocyanate (FITC) or phycoerythrin (PE). PE labeled isotype control lgG1 polyclonal antibodies were obtained from Becton Dickinson, Inc. (San Jose).

EXAMPLE 1

Preparation of Density Gradient Solution

The OCS particle-based density gradient material prepared as described under "Materials" above was diluted in phosphate buffered saline (PBS) to provide a suspension having a defined osmolality and specific density at pH 7.4, as indicated.

The OCS particle-based density gradient material was diluted in water to the approximate specific density required. Solid salts were added to provide a final physiological salt solution (physiological saline or Dulbecco's phosphate buffered saline; Gibco). The suspension was supplemented with different final concentrations (0%–10% w/w) of polyvinylpyrrolidone (PVP-10) by adding the solid powder adjusted for the density of the final suspension. The diluted suspension was finally sterilized by ionizing irradiation (gamma irradiation and E-beam, 2.5–3.5 megaRads; Isomedix, Morton Grove, Ill.), autoclaving (15 min. at 120° C.) or filtration through a 0.2 micron filter according to standard methods known in the art and used at room temperature.

EXAMPLE 2

Preparation of Hematopoietic Progenitor Cells

A. Blood Cell Mixtures

Peripheral blood mononuclear cells (PBPC) were collected by apheresis from non-Hodgkins lymphoma (NHL), Hodgkins lymphoma (HL) and breast-cancer patients at the Bone Marrow Transplantation Laboratory at the Stanford University School of Medicine, Palo Alto, Calif., USA. PBPC were mobilized in NHL patients by treatment with cyclophosphamide (4 g/m$^2$, intravenously) followed by granulocyte colony stimulating factor (G-CSF) (10 µg/kg, intravenously, daily). PBPC were mobilized in breast-cancer patients by treatment with etoposide (VP-16; 2 g/m$^2$, intravenously) followed by G-CSF (10 µg/kg, intravenously, daily). PBPC were mobilized in HL patients by treatment with G-CSF alone. The mobilization protocols used are standard protocols known in the art.

Twenty-four hours following the final injection, each patient was subjected to apheresis. PBPC were collected from the apheresed blood according to standard methods.

B. Bone Marrow Cell Mixtures

Bone marrow aspirate cells were layered slowly on an OCS suspension prepared as described above to a density of 1.0685 gr/ml at an osmolality of 280 mOsm/kg H$_2$O. A maximum of 2×10$^9$ cells was layered and processed per centrifuge tube. The tube was centrifuged for 30 minutes at 850×g, at room temperature. Cells from the interface and pellet were collected separately from a cell-trap tube, in accordance with the present invention. Cell fractions were characterized by FACS analysis using FITC- and PE-conjugated anti-CD34 (anti-HPCA-2), anti-CD45 (anti-HLe-1), anti-CD3 (Leu-4) and IgG1 antibodies, obtained from Becton Dickinson, Inc. (San Jose, Calif.). For analysis, cells were labeled with the nuclear dye LDS 751 (Exciton, Inc., Dayton, Ohio). Statistical analysis was performed on 10$^4$ flow events using a FACSCAN system equipped with a LYSYS II program (Becton Dickinson, Inc. (San Jose, Calif.).

EXAMPLE 3

Density Gradient Separation of PBPC

PBPC cells (0.25 ml), collected according to Example 2 and diluted PBS at a concentration of approximately 5×10$^7$ cells/ml) were layered on an OCS particle-based density gradient suspension (15 ml in a 50 ml centrifuge tube). The suspension had a specific density of 1.0605 gr/ml, an osmolality of 280 mOsm/kg H$_2$O and a pH of 7.4. The layering was performed slowly to avoid mixing of the sample with the solution. A maximum of 2×10$^9$ cells was layered per tube. The centrifugation was performed for 30 min. at 850×g at room temperature. To prevent mixing of the cells and the density gradient solution, the centrifuge was stopped without braking force.

Following centrifugation, the cells were divided into a low-density fraction located at the interface and a high-density fraction forming the pellet. Each cell fraction was collected and transferred into another 50 ml polypropylene centrifuge tube. The cells were washed once and stored in Ca$^{++}$ and Mg$^{++}$ free Dulbecco's phosphate buffered saline (D-PBS) at room temperature until further manipulation. The number and functionality of the hematopoietic progenitor cells (CD34 cells) was determined in both cell fractions by FACS analysis and clonogenic assays (CFU) as detailed in Examples 5 and 6, below.

EXAMPLE 4

Effect on Cells of Mixing with Silanized Colloidal Silica Particles

Assessment of the effect of mixing and subsequent incubation of human peripheral blood in silanized colloidal silica particle-based density gradient solutions was carried out by one or more of the methods described below.

After the respective incubations as detailed below, the cells were collected and washed once with PBS. Their ability to form hematopoietic colonies (CFU-E, BFU-E, CFU-GM and CFU-GEMM), according to methods known in the art, and as described in Example 6, below, was screened at the end of each method. In carrying out experiments, Methods 1, 3, and 5 are control incubation conditions for Methods 2, 4, and 6, respectively.

Method 1

An aliquot containing 10$^7$–10$^8$ cells in 5 ml of 1×D-PBS (Ca$^{++}$, Mg$^{++}$ free) was added to a 15 ml polypropylene centrifuge tube.

Initial cell number was noted. The cells were incubated for 30 minutes at room temperature with gentle mixing at 15 minute intervals.

Method 2

An aliquot containing 10$^7$10$^8$ cells in 5 ml of OCS density gradient suspension was added to a 15 ml polypropylene centrifuge tube. Initial cell number was noted. The cells were incubated for 30 minutes at room temperature with gentle mixing at 15 minute intervals.

Method 3

An aliquot containing 10$^7$–10$^8$ cells in 5 ml 1×D-PBS (Ca$^{++}$, Mg$^{++}$ free) was placed in a 15 ml polypropylene centrifuge tube. Initial cell number was noted. The cells were incubated for 30 minutes at room temperature, with gentle mixing at 15 minute intervals. The cell mixture was then centrifuged at 550×g for 10 minutes. Following centrifugation, the supernatant was discarded and the cell pellet was resuspended in 5 ml of Iscove's medium supplemented with 10% fetal calf serum. The cell mixture was then incubated for 24 hours at room temperature.

Method 4

An aliquot containing $10^7$–$10^8$ cells in 5 ml OCS density gradient suspension was placed in a 15 ml polypropylene centrifuge tube. Initial cell number was noted. The cells were incubated for 30 minutes at room temperature, with gentle mixing at 15 minute intervals. The cell mixture was then centrifuged at 550×g for 10 minutes. Following centrifugation, the supernatant was discarded and the cell pellet was resuspended in 5 ml of Iscove's medium supplemented with 10% fetal calf serum. The cell mixture was then incubated for 24 hours at room temperature.

Method 5

An aliquot containing $10^7$–$10^8$ cells in 5 ml of 1×D-PBS ($Ca^{++}$, $Mg^{++}$ free) supplemented with 10% fetal calf serum was added to a 15 ml polypropylene centrifuge tube. Initial cell number was noted. The cell mixture was then incubated for 24 hours at room temperature.

Method 6

An aliquot containing $10^7$ to $10^8$ cells in 5 ml of OCS density gradient suspension supplemented with 10% fetal calf serum was added to a 15 ml polypropylene centrifuge tube. Initial cell number was noted. The cell mixture was then incubated for 24 hours at room temperature.

EXAMPLE 5

Staining and Quantification of $CD34^+$ Cells by FACS $CD34^+$ cell quantity was determined by Fluorescence Activated Cell Sorting (FACS) after the cells were labeled with a nuclear dye and mAbs directed to CD34 and CD45. The percentage of CD34 cells present was determined in the gate of nucleated cells. This approach was chosen to avoid interference of non-nucleated particulate material with the accuracy of CD34 cell analysis in the FACS.

A suspension of $2\times10^7$ cells/ml was made, using $Ca^{++}$ and $Mg^{++}$ free D-PBS as diluent. Fifty microliters of this cell suspension containing $1\times10^6$ cells was added to each well of a 96-well microtiter plate. Fifty microliters of a 20% heat inactivated rabbit serum/D-PBS solution and 10 microliters of 10 µg/ml LDS 751 (nuclear staining dye) in D-PBS solution were also added to each well, followed by mixing. The plate was covered with foil and incubated for 30 minutes at room temperature. To each control well, was added 10 microliters IgG1-PE. To each test well, was added 10 microliters Anti-CD34-PE, followed by mixing. The plate was covered with foil and incubated for 15 minutes at 4° C. The plate was then centrifuged at 850×g for 5 minutes at 4° C. The supernatant was then removed by flicking.

Each cell pellet was resuspended in 200 µl of cold (4° C.) 1×DPBS ($Ca^{++}$ and $Mg^{++}$ free). The plate was then centrifuged at 850×g for 5 minutes at 4° C., and the resulting supernatant was removed by rapid flicking of the plate. Each cell pellet was resuspended in 50 µl 20% heat inactivated rabbit serum solution. anti-CD45-FITC (10 µl) was added to each control and test well and mixed. The plate was covered with foil and incubated for 30 minutes at 4° C. One hundred microliters of cold (4° C.) 1×D-PBS ($Ca^{++}$ and $Mg^{++}$ free) was then added to all control and test wells, and the plate was centrifuged at 850×g for 5 minutes at 4° C. The plate was flicked rapidly to remove the supernatants, and each cell pellet was resuspended in 200 µl cold (4° C.) 1×D-PBS ($Ca^{++}$ and $Mg^{++}$ free). The plate was centrifuged at 850×g for 5 minutes at 4° C., then flicked rapidly to remove supernatant. Each cell pellet was then resuspended in 200 ml 1% paraformaldehyde (4° C.). The plate was then covered with foil and stored at 4° C. until FACS analysis of the samples.

FACS analysis was performed on $10^4$ flow events using a FACSStar Plus system equipped with a LYSYS 11 statistical analysis program (Becton Dickinson, Inc.). For purposes of analysis, a gate (Region 1) was placed around the nucleated cells determined by LDS 751 staining in FL3 in order to gate out the red cells, platelets and debris. FL1 and FL2 were displayed as a dot plot using Region 1. A gate (Region 2) was placed around the cell population that stained with both the anti-CD45 and anti-CD34 monoclonal antibodies. For purposes of analysis, the percentage of cells that stain with the anti-CD34 (FL2) and anti-CD45 (FL1) monoclonal antibodies was determined in Region 2. This represents the number of CD34 positive cells as a percentage of the total number of nucleated cells. The total number of CD34 positive cells was determined in the unprocessed sample and in the cell fraction obtained from the interface and the pellet after processing of the PBPC samples in the density gradient solution.

EXAMPLE 6

Colony Forming (CPU) Assay

The functional characteristics of the $CD34^+$ cells in a cell sample were determined by the colony formation (CFU) assay. This assay provides quantitation of the number of committed hematopoietic progenitor cells in the cell solution.

Cells were diluted to a concentration of $10^5$ cells in 2 mL commercially prepared semi-solid methyl cellulose containing various colony stimulating factors and erythropoietin (MethoCult™ H4433 medium, Terry Fox Laboratories, Vancouver).

After 14 days of culture at 37° C., the erythroid (CFU-E, BFU-E), granulocyte/macrophage (CFU-GM) and mixed (CFU-GEMM) colonies were counted under an inverted microscope (40×), according to standard methods. The total number of CFU present in a cell mixture was defined by summation of the different types of colonies counted.

EXAMPLE 7

Determination of Total Cell Recovery

The percent cell recovery was determined by the formula:

$$\% \text{ Recovery} = 100 \times \frac{\text{Nr. of cells after manipulation}}{\text{Nr. of cells at start}}$$

The percent CD34 cell recovery was determined by the formula:

$$\% \text{ Recovery} = 100 \times \frac{\text{Nr. of } CD34^+ \text{ cells after manipulation}}{\text{Number of } CD34 \text{ cells at start}}$$

The percent clonogenic cell recovery was determined by the formula:

$$\% \text{ Recovery} = 100 \times \frac{\text{Nr. clonogenic cells } (CFU) \text{ after manipulation}}{\text{Nr. of clonogenic cells } (CFU) \text{ at start}}$$

EXAMPLE 8

Effect of Radiation on hematopoietic cell recovery

The effect of irradiated organosilanized colloidal silica particles on hematopoietic cell integrity was tested, using the protocol described in Example 4 as "Methods 3 and 4." OCS particles, OCS particles supplemented with 0.5% PVP, or PBS supplemented with 0.5% PVP (5 ml total volume) was irradiated in a 50 ml conical centrifuge tube by a dose of gamma irradiation (2.5–3.5 megaRads). In these experiments, the density of the OCS particle suspension used was 1.0605 gr/ml, a density that is lower than that of the cells to be isolated, to facilitate subsequent pelleting and quantification of cells present in the tube.

An aliquot containing $3 \times 10^7$ PBPC cells, isolated as described in Example 1, was added to each tube, and initial cell number was noted. The cells were incubated for 30 minutes at room temperature, with gentle mixing at 15 minute intervals. The cell mixture was then centrifuged at 550×g for 10 minutes. Following centrifugation, the supernatant was discarded and the cell pellet was resuspended in 5 ml of Iscove's medium supplemented with 10% fetal calf serum. The cell mixture was then incubated for 24 hours at room temperature, and then tested in the CFU assay described in Example 6. Results of this experiment are shown in FIG. 1.

EXAMPLE 9

Sterile Centrifugation Kit

A sterile centrifuge kit was prepared for separating CD34+ hematopoietic progenitor cells from peripheral blood mononuclear cells (PBPC) as follows: An OCS particle-based density particle density gradient suspension was prepared as described in Example 1. A stock solution was prepared by mixing 12 parts of the OCS particle suspension with 1 part of 10×calcium and magnesium-free phosphate buffered saline (PBS) and concentrated PVP (PVP-10; Sigma) to prepare a medium having a density of 1.0605±0.0005 gr/ml, pH 7.4, an osmolality 280 mOsm/Kg H$_2$O, and a concentration of 4% PVP. The density of the OCS particle solution may be adjusted on a densitometer to precisely define its accuracy up to at least the fourth decimal place.

Fifteen milliliters of this suspension was added to a polypropylene 50 ml conical centrifuge tube (Baxter). The tube was sealed with the standard screw cap supplied with the tube. The tube and its contents were then exposed to gamma irradiation 2.5–3.5 megaRads by placing it in a chamber. The resulting sterile centrifuge kit was used in separating CD34+ cells from PBPC, as described in Example 4 herein.

While the invention has been described with reference to specific methods and embodiments, it will be appreciated that various modifications and changes may be made without departing from the invention.

It is claimed:

1. A composition for use in cell separation, comprising a silanized silica particle suspension treated with ionizing radiation in the presence of at least about 0.05% polylactam.

2. The composition of claim 1, wherein said silanized silica particle is an organosilanized colloidal silica particle.

3. The composition of claim 1, wherein said polylactam is polyvinylpyrrolidone present at a concentration between about 0.1 and about 10 percent.

4. The composition of claim 1, wherein said particle is a microsphere having a diameter of between about 0.003 and 50 microns.

5. The composition of claim 1, wherein said ionizing radiation is selected from gamma radiation and E-beam radiation.

6. The composition of claim 1, for use in isolating a selected rare blood cell from a cell mixture, wherein said organosilanized colloidal silica particle suspension has a specific density approximately equal to that of said selected cell.

7. The composition of claim 6, wherein said rare blood cell is a hematopoietic progenitor CD34+ cell, said cell mixture comprises peripheral blood mononuclear cells, and said organosilanized colloidal silica particle suspension has a specific density of 1.0605 gr/ml at an osmolality of 280±10 mOsm/kg H$_2$O.

8. The composition of claim 6, wherein said rare blood cell is a hematopoietic progenitor CD34+ cell, said cell mixture comprising bone marrow cells, and said organosilanized colloidal silica particle suspension has a specific density of 1.0685 gr/ml at an osmolality of 280±10 mOsm/kg H$_2$O.

* * * * *